United States Patent [19]
Almeida et al.

[11] Patent Number: 6,094,262
[45] Date of Patent: Jul. 25, 2000

[54] HIGH TEMPERATURE DIFFERENTIAL REFRACTOMETRY APPARATUS

[75] Inventors: Neal Belarmino Almeida, Cumberland, R.I.; Jose Luis deCorral, Hopedale, Mass.

[73] Assignee: Waters Investments Limited

[21] Appl. No.: 09/258,780

[22] Filed: Feb. 26, 1999

[51] Int. Cl.[7] .................................................. G01N 21/41
[52] U.S. Cl. ............................................................ 356/130
[58] Field of Search .................................... 356/128, 130, 356/131, 132, 134

[56] References Cited

U.S. PATENT DOCUMENTS

| | | | |
|---|---|---|---|
| 4,284,352 | 8/1981 | Carson et al. | 356/134 |
| 5,398,110 | 3/1995 | Kitaoka | 356/130 |

OTHER PUBLICATIONS

Eric Fortheringham et al., reprinted from *American Laboratory*, "An integrated GPC–SEC system for room–temperature and high–temperature polymer characterization", Feb. 1998, 9 pages total.

*Primary Examiner*—Hoa Q. Pham
*Assistant Examiner*—Michael P. Stafira
*Attorney, Agent, or Firm*—Brian Michaelis; Anthony J. Janiuk

[57] ABSTRACT

A differential refractometry apparatus that maintains optimal optical alignment of components while accurately providing differential refractometry measurements at elevated temperatures. The differential refractometry apparatus has a first thermal zone, a thermal isolation zone and a second thermal zone. The first thermal zone is configured to be located in an oven and exposed to higher temperatures. The thermal isolation zone is located adjacent to the first thermal zone and acts as a barrier to the conduction of heat from the first thermal zone into the second thermal zone. The second thermal zone is at a relatively lower temperature than the first thermal zone and its temperature is regulated using a thermal electric cooler located at its base. A flow cell, a mirror which reflects the incoming light beam, and an imaging lens are located in the first thermal zone. An LED and a photodiode detector are located in the second thermal zone and are encased in thermally stable blocks with low coefficients of thermal expansion. The LED sends a light beam up through the thermal isolation zone and into the first thermal zone. The light beam passes through the sample and gets reflected by the mirror. The light beam passes through the sample a second time. The light beam then passes through an imaging lens before traveling back to the photodiode in the second thermal zone. In this manner the optimal optical geometry is preserved while allowing analyses to be conducted with the sample at elevated temperatures.

16 Claims, 5 Drawing Sheets

HIGH TEMPERATURE DIFFERENTIAL REFRACTOMETRY APPARATUS

FIELD OF THE INVENTION

The present invention relates to differential refractometry instrumentation, and more particularly to a method and apparatus implementing systems conducting differential refractometry of samples at high temperatures.

BACKGROUND OF THE INVENTION

The ability of a medium to refract light is its refractive index ("RI"). RI is the ratio of the velocity of light in a vacuum to the velocity of light in a medium. It is a physical property of the medium and is represented by a dimensionless integer "n". Differential refractometry is the art of measuring small differences in RI between a reference solution and a sample solution. The difference in RI is referred to as "Δn". Δn is measured in RI units ("RIU").

Differential refractometers in the prior art generally consist of a light emitting diode (LED), a flow cell containing a sample side and a reference side, and a dual element photodiode detector. As illustrated in FIG. 1, known differential refractometers utilizing a dual pass optics bench contain a mirror which reflects the light causing the light beam to pass through the flow cell twice before reaching the photodiode.

After the light beam passes through the flow cell the second and final time, it passes through an imaging lens and then falls upon the dual element photodiode. When the flow cell contains just solvent, the position of the light beam is centered on the elements of the photodiode as shown in FIG. 2a. This position of the beam creates a baseline signal. When sample is inserted into the flow-cell, light beam is refracted further, causing a deflected image on the photodiode as illustrated in FIG. 2b. The deflected image creates a signal that differs from the base-line signal. The changing signal from the photodiode results in a change in the output voltage of the refractometer. An integrator or chart recorder then registers the changes in output voltage as peaks on a chromatogram.

One factor that always creates issues in refractometry is temperature. The sample has to be maintained in a very thermally stable environment. Even slight changes or variations in temperature affect the density of the sample thereby changing its refractive index. Temperature also poses problems in elevated temperature polymer characterization and other high temperature analyses because the LED and the photodiode detector are electronic devices which generally cannot withstand very high temperatures.

It is generally known in the industry that taking one or both of the LED or the photodiode detector out of the high thermal environment is a solution to problems caused by high temperatures. However, taking both devices out of the high temperature thermal environment creates alignment, reliability and cost issues, and the refractometer is no longer a self contained unit. Taking one or both of the LED or photodiode detector out of the high thermal environment is usually accomplished by means of fiber optic cables that complicate the optical alignment. The fiber optic cables can degrade over time due to temperature and mechanical stress, causing reductions in light transmission. In addition to the cost of fiber optic cables, there are other costs associated with mounting parts at the fiber optic cable ends.

A known refractometer implementation aimed at allowing analyses at high temperatures is the Waters 150C Refractometer available from Waters Corporation, Milford, Mass. In this implementation, the light source, a tungsten lamp, is positioned outside of the high thermal environment while the photodiode detector is positioned within the high thermal environment to maintain the optical geometry of the system. As a result the Waters 150C Refractometer can only be used for analyses at 150° C. or below or the integrity of the electronic photodiode detector will be compromised. Also, the signal to noise performance is generally negatively affected at temperatures above 100° C. due to increased photodiode electrical noise at such elevated temperatures.

SUMMARY OF THE INVENTION

The present invention provides a differential refractometry apparatus that maintains optimal optical alignment of components while accurately providing differential refractometry measurements at elevated temperatures.

According to the invention, the differential refractometry apparatus comprises a first thermal zone, a thermal isolation zone and a second thermal zone. The first thermal zone is configured to be located in an oven and exposed to higher temperatures. The thermal isolation zone is located adjacent to the first thermal zone and acts as a barrier to the conduction of heat from the first thermal zone into the second thermal zone. The second thermal zone is at a relatively lower temperature than the first thermal zone and its temperature is regulated using a thermal electric cooler located at its base. In an illustrative configuration the refractometer is disposed vertically so that the first thermal zone is located above the thermal isolation zone which is above the second thermal zone.

A flow cell, a mirror which reflects the incoming light beam, and an imaging lens are located in the first thermal zone. An LED and a photodiode detector are located in the second thermal zone and are encased in thermally stable blocks with low coefficients of thermal expansion. The LED sends a light beam up through the collimating lens and then through the thermal isolation zone and into the first thermal zone. The light beam passes through the flow cell and gets reflected by the mirror. The light beam passes through the flow cell a second time. The light beam then passes through the imaging lens before traveling back to the photodiode in the second thermal zone. In this manner the optimal optical geometry is preserved while allowing an analyses to be conducted with the sample at elevated temperatures.

Features of the invention include RI measurements at elevated temperatures, preservation of the optimal geometric alignment of the optical devices, and an accurately controlled dual temperature zone minimizing RI noise and drift thereby improving the refractometer detector's precision. The present invention is designed to minimize temperature fluctuations within each of the two thermal zones as well as to ensure that the temperature of the zones relative to each other remains constant.

BRIEF DESCRIPTION OF THE DRAWING

The foregoing and other features and advantages of the present invention will be more fully understood from the following detailed description of illustrative embodiments, taken in conjunction with the accompanying drawing in which.

DETAILED DESCRIPTION

Figure 1:
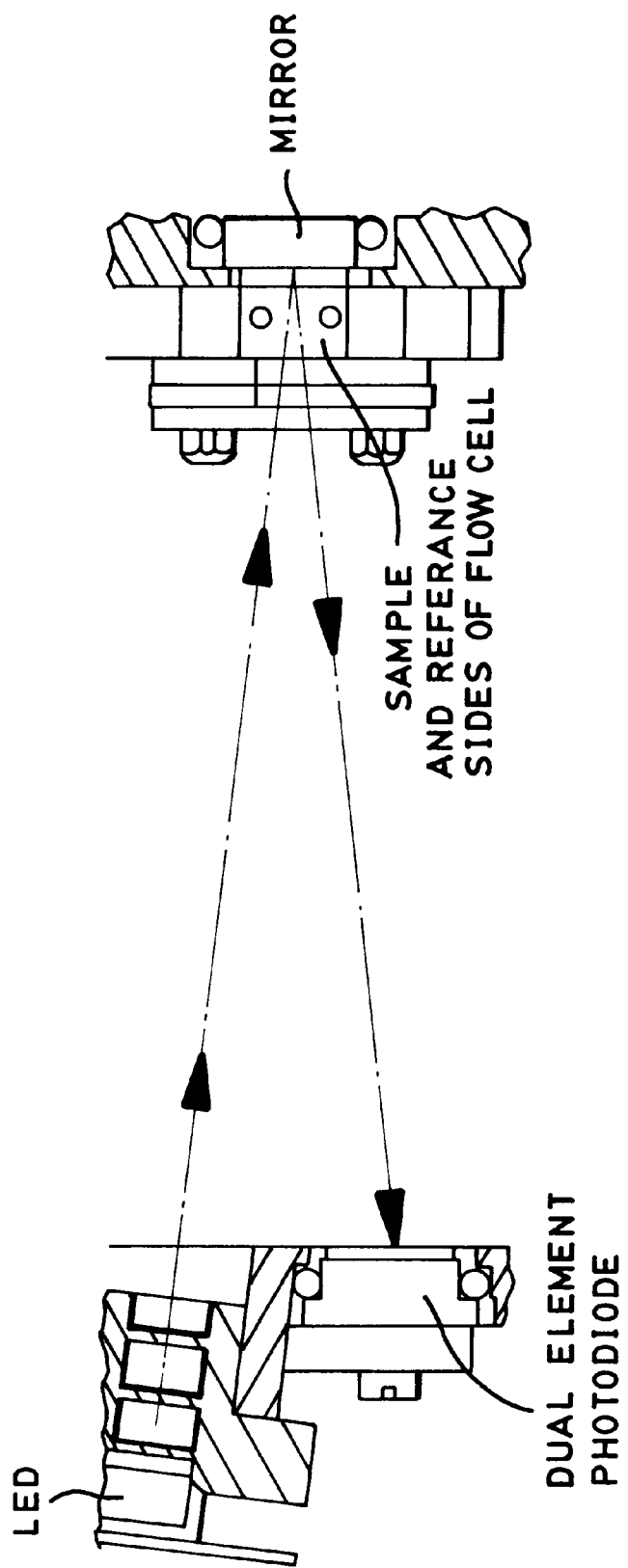
FIG. 1 is a general illustration of the path a light beam follows in a differential refractometry apparatus according to the prior art.
Figures 2A, 2B:
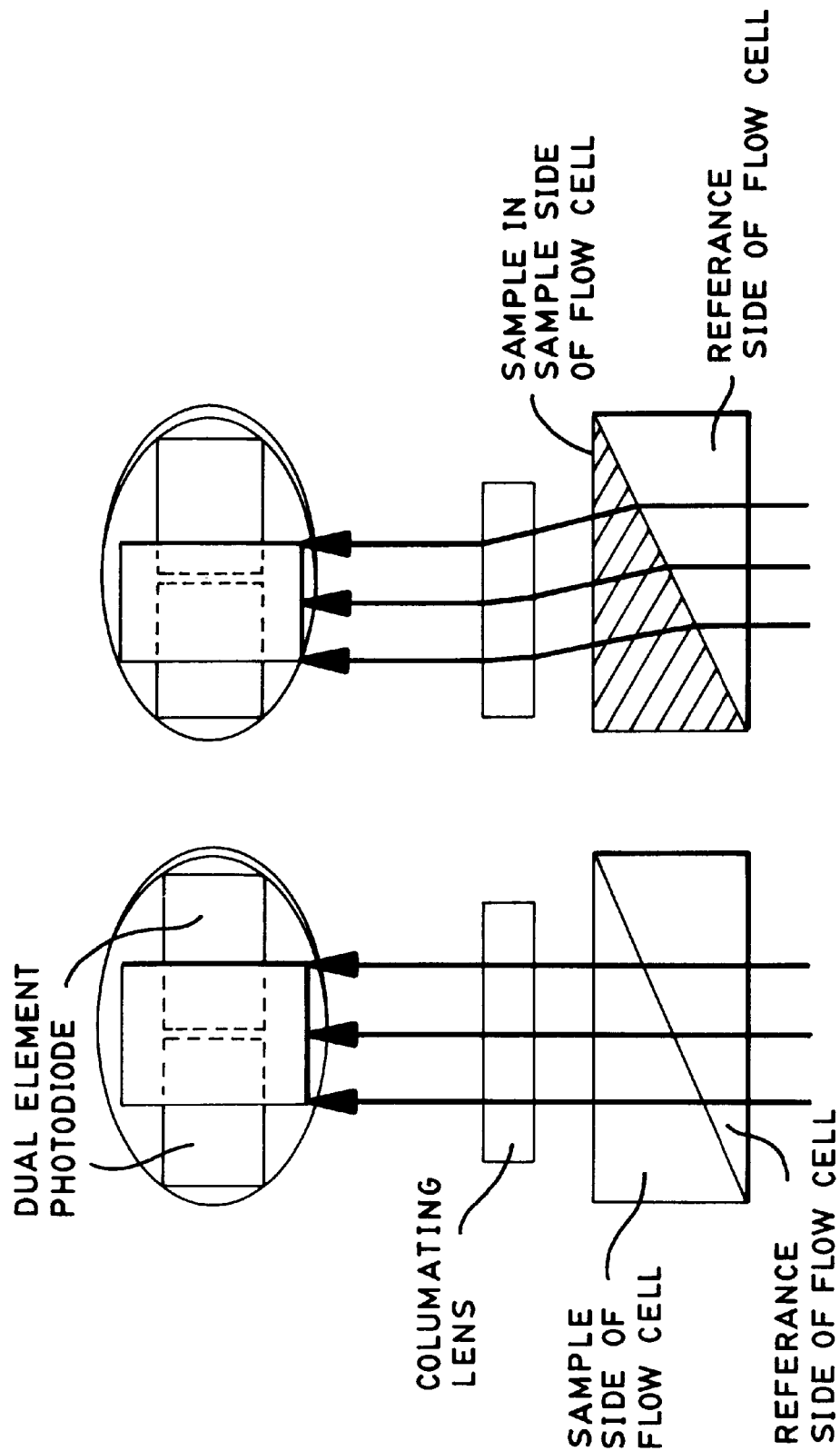
FIG. 2a illustrates the position of the light beam on the elements of a dual element photodiode when there is no sample in the flow cell according to the prior art.
FIG. 2b illustrates how the light beam of FIG. 2a is refracted creating a deflected image on the photodiode when sample is inserted into the flow cell.
Figure 3:
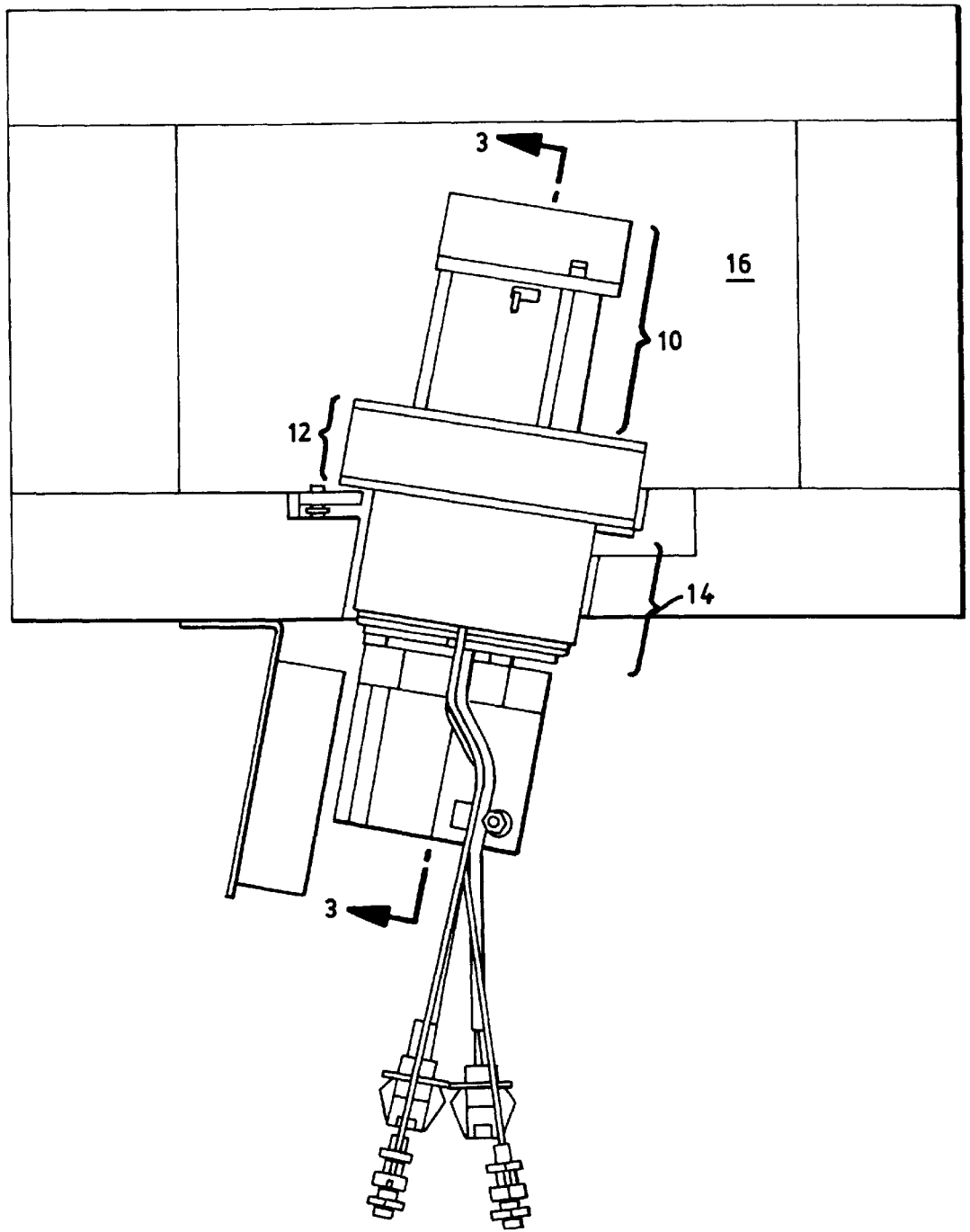
FIG. 3 is a side view of a differential refractometer according to the invention installed in an oven.

The present invention, referring to FIG. 3, comprises a differential refractometry apparatus containing a first thermal zone 10, a thermal isolation zone 12 and a second thermal zone 14. The three zones are disposed substantially vertically in an illustrative configuration so that the first thermal zone 10 is located above the thermal isolation zone 12 which is above the second thermal zone 14.

Figure 4:
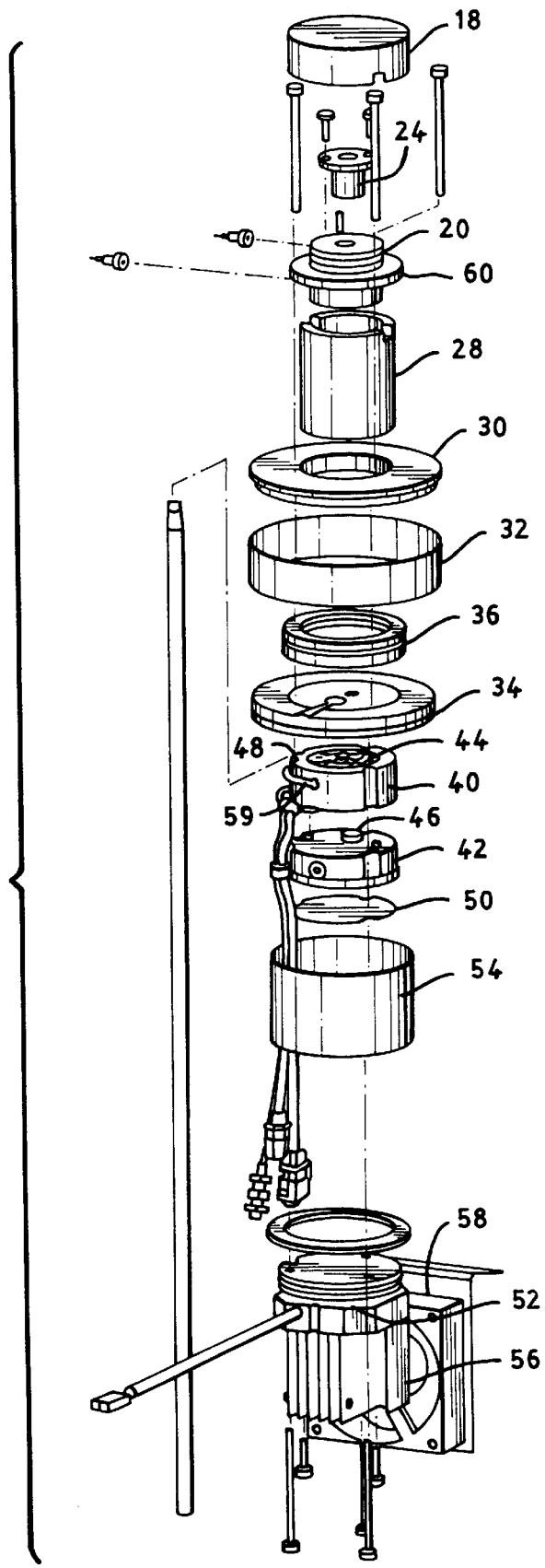
FIG. 4 is an exploded view of the components of the high temperature differential refractometry apparatus according to the present invention.
Figure 5:
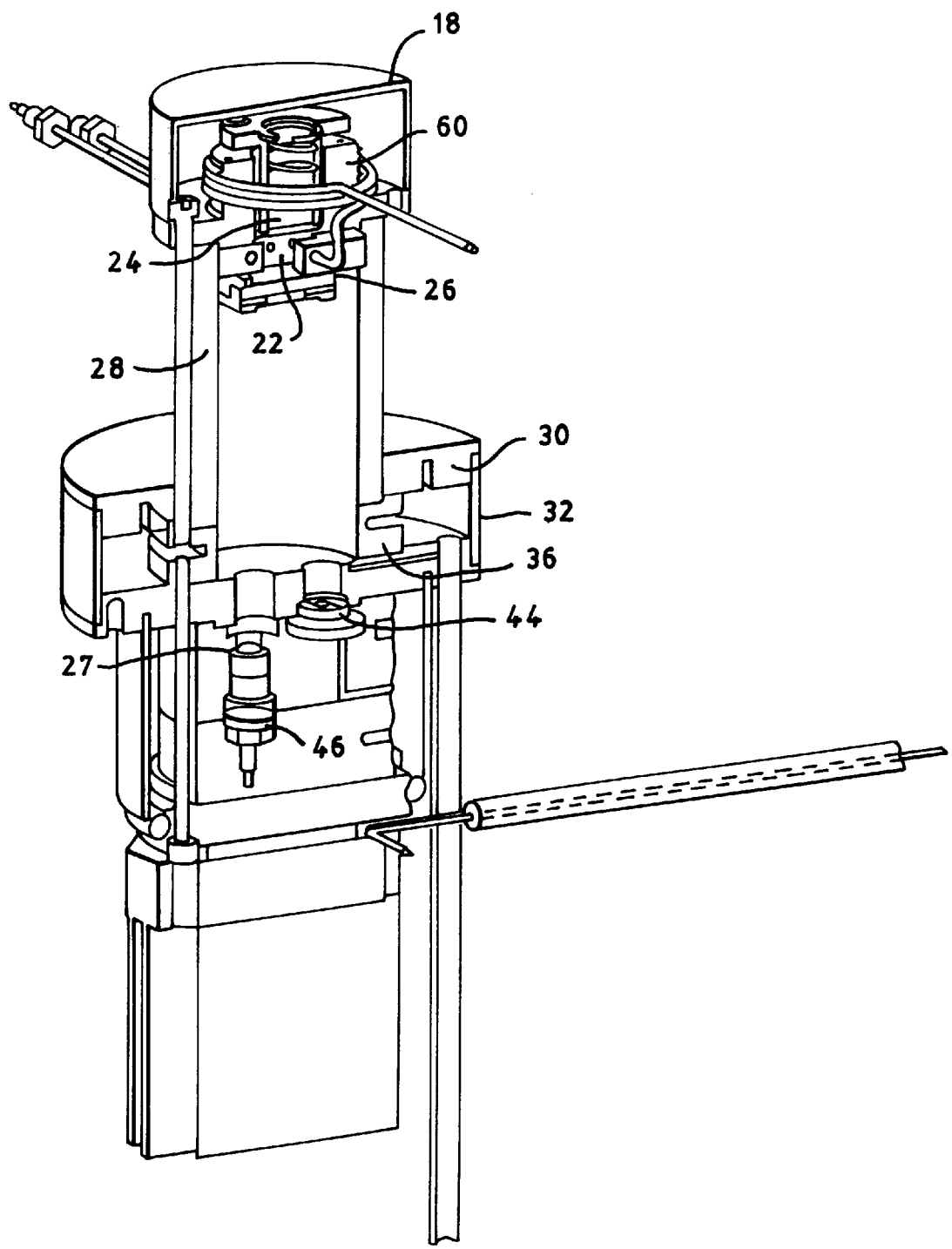
FIG. 5 is a cross-section taken along a vertical plane 3—3 (FIG. 3) of the differential refractometry apparatus according to the present invention.

As illustrated in FIGS. 3–5, the first thermal zone is located in an oven 16 with an elevated internal temperature. The first thermal zone of the refractometer according to the invention comprises a shield 18, seen best in FIG. 4, which covers the mirror 24, the flow cell body 60 and a stainless steel tube heat exchanger 20 through which sample is transmitted to a flow cell 22, as known in the art. The stainless steel tube heat exchanger is wrapped around the outside diameter of a metallic cylinder portion of the flow cell body a plurality of times. This allows the sample to attain the temperature of the flow cell body before it enters the flow cell.

A mirror 24 for reflecting light, is configured in a cylindrical housing which is inserted into a counter bore of the flow cell body. The mirror is anchored by a plurality of screws. The mirror 24 is disposed proximate to the flow cell 22. The flow cell contains first and second compartments (not shown). The first compartment contains a reference solution, while various sample solutions are cycled through the second compartment. In this illustrative embodiment, the flow cell is made of fused quartz.

An imaging lens 26 (best seen in FIG. 5) is located adjacent to the flow cell 22 and focuses rays of light reflecting off of the mirror 24 into the dual element photodiode detector 44.

A cylindrical insulation body 28 abuts against an end surface of the flow cell body 60. The cylindrical insulation body 28 in this illustrative embodiment is made of a machinable, fully-dense ceramic material, such as AREM-COLOX 502 series ceramics. Such a material has low thermal conductivity, and in the illustrative embodiment, a low coefficient of thermal expansion. The cylindrical insulation body therefore minimizes the transfer of heat by conduction from the first thermal zone, which is at an elevated temperature, to the second thermal zone.

The cylindrical insulation body 28 is effectively a portion of the thermal isolation zone 12. An insulation shield 30, forming another portion of the thermal isolation zone 12, engages an end of the cylindrical insulation body 28 distal to the flow cell 22. The insulation shield 30 is made of Teflon, which is a material with low thermal conductivity. A thermal shield 32 engages a portion of the insulation shield 30. The thermal shield in turn engages with an insulator plate 34. The insulator plate 34 includes orifices for passage of light to and from the mirror 24. The thermal shield 32 and the insulator plate 34 are made of polyphenylene sulphide (PPS) which has a low thermal conductivity.

A chassis component 36, configured with a groove to minimize thermal conduction, is encapsulated by the thermal shield 32, insulation shield 30, insulator plate 34 and insulation body 28.

The second thermal zone 14 contains a first thermally stable block 40 and a second thermally stable block 42. The first thermally stable block 40 contains a dual element photodiode detector 44, a void 48 for passage of light therethrough, and embedded in the block next to the dual element photodiode detector, a temperature sensor such as a thermistor 59. The thermistor allows for monitoring and control of the block temperature. The second thermally stable block 42 contains an LED 46. The blocks, in this illustrative embodiment, are made of INVAR, a 36% nickel-iron alloy having a very low coefficient of thermal expansion. The INVAR blocks do not undergo dimensional changes with changes in temperature and, therefore, make an ideal material which substantially ensures the stability of the electrical devices. The first thermally stable block 40 and the second thermally stable block 42 are electrically connected, and both are electrically insulated from the remaining assembly by a mica sheet 50. A shield 54 is configured to house the thermally stable blocks 40, 42, to prevent temperature fluctuations due to moving air.

The second thermal zone is configured so that its base contains a thermoelectric cooler (TEC) 52. The TEC is a solid state heat pump, such as a MELCOR TEC, that utilizes the Peltier effect for heat exchange. A heat sink 56 is adjacent to the TEC which is in thermally conductive communication with the thermally stable blocks. Accordingly, heat is conveyed away from the electronic devices in the thermally stable blocks 40, 42, and toward the heat sink 56.

That is, during operation, DC current flows through the TEC causing heat to be transferred from one side of the TEC to the other. As a result, a hot side and a cold side are created in the TEC. The TEC is configured so that the cold side is adjacent to the thermally stable blocks 40, 42, while the hot side is exposed to the heatsink 56 which dissipates the heat. A fan 58 is placed adjacent to the heatsink to dissipate the heat.

There are many advantages to using a TEC to regulate and control the temperature of the second thermal zone. The TEC is small, lightweight, and completely silent. It does not produce any vibrations that might adversely affect the optics. With no moving mechanical parts, the TEC is extremely reliable and thus provides a cost effective way of regulating the temperature of the second thermal zone. Finally, the TEC provides extremely precise temperature control which, as mentioned earlier, is crucial to obtaining accurate RI readings.

The differential refractometer according to the invention is used for high temperature analysis of selected samples. The refractometer is configured with the first thermal zone 10 and a significant portion of the thermal isolation zone 12 disposed in an elevated temperature environment, e.g. oven. The second thermal zone 14 is typically subject to an ambient temperature environment (see FIG. 3).

Light is emitted from the LED 46 and passes through a collimating lens 27 and a mask (not shown) in the first thermally stable block 40. The light traverses the insulation body 28 and passes through the sample and reference chambers of the flow cell 22, which are maintained at an elevated temperature in the oven. The light having passed through the sample/reference, is reflected by the mirror 24. After passing through the sample/reference a second time, the light is focused by the imaging lens 26 adjacent to the flow cell body 60. The reflected light (which is refracted to some extent as a function of the sample under analysis), impinges upon the photodiode detector 44 in the first thermally stable block 40. According to the invention the electronic devices (i.e., LED 46 and detector 44) are maintained at a lower and relatively safe temperature with respect to the first thermal zone 10 temperature. The electronic devices are maintained in a thermally stable condition via the containment in the thermally stable blocks, in thermally conductive communication with the TEC 52. Accordingly, extremely stable and reproducible high temperature analysis is performed. It should be appreciated that significant temperature stability is achieved by orienting the refractometer according to the invention in a vertical manner, which avoids introduction of optical aberrations due to convective air movements. The refractometer is slightly tilted from the vertical position to help purge air bubbles from the sample and reference sides of the flow cell.

Although the refractometer described herein includes an insulation body 28 formed of a low thermal conductivity ceramic, it should be appreciated that other low conductivity materials could be used such as machinable or non-machinable ceramics, PPS, PEEK, RYTON, glass, high density PYROPEL or the like.

While the thermal isolation zone 12 described herein specifically includes an insulation shield, thermal shield, a chassis portion with a groove and an insulator plate, it should be appreciated that other combinations of elements could be configured to provide thermal isolation. For example, the chassis portion (with or without a groove) could be omitted, and/or the thermal shield could be omitted or alternatively configured. Similarly, such components could be made from materials with low thermal conductivity (i.e., other than PPS), such as PEEK, high density PYROPEL, Teflon, ceramic or the like.

Although INVAR, a material with a low coefficient of thermal expansion, is specified for forming thermally stable blocks 40, 42, flow cell body 60 and chassis 36, it should be appreciated that other materials could be used, such as stainless steel or the like.

While a TEC is used to exchange heat in the second thermal zone, it should be appreciated that other heat exchange devices could be implemented, such as liquid recirculation through a heat exchanger, variable air flow cooling or the like.

Although a vertical orientation is described for the refractometer implemented herein, it should be appreciated that alternative orientations can be implemented such as a horizontal orientation and/or an inverted orientation wherein the orientation of the thermal zones is inverted. Similarly, it should be appreciated that a refractometer could be implemented without a mirror. That is, in an alternative implementation the light source and the photodiode detector could be disposed in extreme ends of the refractometer in two different and separate "second" thermal zones (i.e. low temperature zone). Each of these "second" thermal zones would be separated from the first thermal zone by a respective thermal isolation zone.

Although the invention has been shown and described with respect to exemplary embodiments thereof, various other changes, omissions and additions in the form and detail thereof may be made therein without departing from the spirit and scope of the invention.

What is claimed is:

1. A differential refractometry detection apparatus including a flow cell, a light source and a light detector, comprising:
    a first thermal zone containing said flow cell at a first temperature;
    a thermal isolation zone disposed adjacent to said first thermal zone; and
    a second thermal zone containing at least one of said light source and said light detector at a second temperature, said second temperature being lower than said first temperature, said second thermal zone disposed adjacent to said thermal isolation zone.

2. The apparatus of claim 1 wherein said thermal isolation zone includes components made of material having low thermal conductivity and substantially thermally isolates said second thermal zone from said first thermal zone.

3. The apparatus of claim 1 wherein said first thermal zone further includes at least one of a mirror which reflects an incoming light beam from said light source, and an imaging lens.

4. The apparatus of claim 1 wherein said light source is an LED disposed in said second thermal zone.

5. The apparatus of claim 1 wherein said light detector is a dual element photodiode detector located in said second thermal zone.

6. The apparatus of claim 1 wherein said light source is an LED and said light detector is a dual element photodiode detector, and said second thermal zone further includes at least one thermally stable block with a low coefficient of thermal expansion in which at least one of said LED and said dual element photodiode detector are embedded.

7. The apparatus of claim 1 wherein said thermal isolation zone includes an annular chassis element having a groove disposed therein to limit thermal conduction.

8. The apparatus of claim 1 wherein said first thermal zone is configured to be located in an oven and exposed to temperatures in excess of 150 degrees centigrade.

9. The apparatus of claim 1 wherein temperature in said second thermal zone is regulated using a heat exchanging device.

10. The apparatus of claim 9 wherein said heat exchanging device is a thermal electric cooler, and said second thermal zone includes at least one thermally stable block in which at least one of said light source and said light detector is disposed and which further has a temperature sensor disposed therein for monitoring and control of temperature of said at least one thermally stable block using said thermal electric cooler.

11. The apparatus of claim 9 wherein a heat sink is disposed proximate to said heat exchanging device.

12. The apparatus of claim 1 wherein said refractometer apparatus is disposed vertically so that said first thermal zone is located above said thermal isolation zone which is above said second thermal zone.

13. The apparatus of claim 1 wherein said second thermal zone includes a collimating lens.

14. A differential refractometry detection apparatus, comprising:
    a first thermal zone comprising a flow cell, a mirror and a first lens, substantially maintained at a first temperature in an elevated temperature environment;
    a thermal isolation zone disposed adjacent to said first thermal zone, said thermal isolation zone including at least one component made of material having low thermal conductivity; and
    a second thermal zone containing a light source and a light detector at a second temperature, said second temperature being lower than said first temperature, said second thermal zone disposed adjacent to said thermal isolation zone and including a heat exchange device.

15. The apparatus of claim 14 wherein said light source is an LED and said light detector is a dual element photodiode detector.

16. The apparatus of claim 14 wherein said heat exchanging device is a thermal electric cooler.

* * * * *